United States Patent [19]

Reimer

[11] Patent Number: 5,206,441
[45] Date of Patent: Apr. 27, 1993

[54] HIGH RATE PROCESS FOR PREPARATION OF CYCLOHEXANOL AND CYCLOHEXANONE

[75] Inventor: Ronald A. Reimer, Orange, Tex.

[73] Assignee: E. I. Du Pont de Nemours and Company, Wilmington, Del.

[21] Appl. No.: 863,737

[22] Filed: Apr. 6, 1992

[51] Int. Cl.$^5$ .............................................. C07C 45/53
[52] U.S. Cl. .................................. 568/342; 568/798
[58] Field of Search ............................... 568/342, 798

[56] References Cited

U.S. PATENT DOCUMENTS

| | | | |
|---|---|---|---|
| 4,238,415 | 12/1980 | Bryan | 568/342 |
| 4,499,305 | 2/1985 | Hermolin | 568/342 |
| 4,543,427 | 9/1985 | Hartig et al. | 568/342 |
| 4,551,553 | 11/1985 | Taylor et al. | 568/342 |
| 4,720,592 | 5/1987 | Besmas et al. | 568/342 |

FOREIGN PATENT DOCUMENTS

7802125  8/1979  Netherlands ..................... 568/342

OTHER PUBLICATIONS

Vogel, "Practical Organic Chemistry", pp. 62-63 (1948).

Primary Examiner—James H. Reamer

[57] ABSTRACT

A process for the conversion of cyclohexyl hydroperoxide to cyclohexanone and cyclohexanol by turbulent high-intensity mixing with aqueous caustic containing a metal salt that accelerates the decomposition of cyclohexyl hydroperoxide.

4 Claims, No Drawings

HIGH RATE PROCESS FOR PREPARATION OF CYCLOHEXANOL AND CYCLOHEXANONE

FIELD OF THE INVENTION

This invention relates to an improvement in the production of cyclohexanol and cyclohexanone by the decomposition of cyclohexyl hydroperoxide.

BACKGROUND OF THE INVENTION

Mixtures of cyclohexanol, cyclohexanone and cyclohexyl hydroperoxide are the reaction product of the air oxidation of cyclohexane. Cyclohexyl hydroperoxide can be hydrogenated to produce cyclohexanone and cyclohexanol; see, for example, U.S. Pat. No. 4,720,592 to Besmar et al., or cyclohexyl hydroperoxide can be decomposed by neutralizing the acids contained in the mixture with an alkali metal hydroxide, and then reacting it with excess free metal hydroxide and metal salts that cause it to decompose to form cyclohexanol and cyclohexanone, but the reaction does not produce these products in quantitative yield and other waste products are also produced: see U.S. Pat. No. 4,720,592, column 1, lines 43-50, and U.S. Pat. No. 4,238,415 to Bryan. Cyclohexanol and cyclohexanone can be further oxidized, for example, with nitric acid, to form adipic acid. Adipic acid is one of the principal ingredients used in the production of nylon.

The use of static mixers in the treatment of air oxidation products of cyclohexane is shown in U.S. Pat. No. 4,720,592 to Besmar et al.

An object of the present invention is to provide a high rate process for decomposing cyclohexyl hydroperoxide to form cyclohexanol and cyclohexanone and only very small amounts of waste products.

SUMMARY OF THE INVENTION

The present invention is a process for the conversion of cyclohexyl hydroperoxide contained in a mixture with cyclohexane, cyclohexanone, cyclohexanol and aqueous caustic, to cyclohexanone and cyclohexanol, which comprise adding a metal salt that accelerates the caustic catalyzed decomposition of cyclohexyl hydroperoxide and subjecting the mixture to turbulent high-intensity mixing to create a dispersed phase drop size of between 50 to 500 microns, for a time of between 3 and 45 seconds (preferably between 3 and 25 seconds) at a temperature between 100 and 140 degrees C., and then subjecting the mixture to a non-turbulent decantation.

Due to the formation of a dispersed phase having a drop size between 50 and 500 microns it is possible to complete the reaction quickly. The reaction speed is increased further if the temperature is at about 120 to 140 degrees C. If decomposition were carried out at this temperature for extended periods of time (a few minutes instead of a few seconds), increased quantities of waste product would be formed.

The turbulent high-intensity mixing is preferably carried out in a static mixer. Suitable mixers are known in the art, e.g., Kenics mixers, see U.S. Pat. No. 3,286,992, or Koch mixers of Lightnin mixers.

Suitable metal salts useful to accelerate decomposition of cyclohexyl hydroperoxide are those where the metal in the salt is selected from the group consisting of cobalt, copper, chromium, iron, and vanadium. Usually the metal salt concentration in the mixture is in the range of about 0.1 to about 50 ppm. by weight of the mixture. Suitable anion of the metal salts include sulfates and acetates. Cobalt sulfate is preferred.

The mixture should contain enough caustic to neutralize acids that were formed during the air oxidation of cyclohexane to form the cyclohexyl hydroperoxide, plus excess free caustic in an amount sufficient to raise the pH of the solution to at least 12 and preferably greater than 13.

The amount of aqueous caustic in the feed to the reaction mixture will normally be about 5 to 30% by weight of the mixture. The aqueous reaction phase will normally contain 3 to 7% free caustic. The aqueous caustic is the dispersed phase when the ingredients are subjected to the mixing step.

After turbulent high-intensity mixing for 3 to 45 seconds, upwards of 90% of the cyclohexyl hydroperoxide will have decomposed. The mixture is then passed to a non-turbulent decantation zone, where the reaction continues as the aqueous phase and organic phase stratify. The aqueous phase is then separated from the organic phase by decantation. The organic phase is usually then subjected to distillation to separate the cyclohexanone and cyclohexanol from the cyclohexane, and the cyclohexanone and cyclohexanol subjected to nitric acid oxidation to form adipic acid.

EXAMPLES

1. A 76 ft. long mixer-reactor system was constructed using ¼" O.D. stainless steel tubing with ten Kenics No. 37-04-065 static mixers installed along its length. Each mixer unit was 7" long with 21 elements. The mixer-reactor was immersed in a 55 gallon oil bath controlled at a temperature of 120° C.

2. Water-washed air oxidized cyclohexane obtained from an operating plant was used with this example. Its composition was:

| | |
|---|---|
| 1.39% | cyclohexyl hydroperoxide |
| 0.09% | dicyclohexyl hydroperoxide |
| 1.00% | cyclohexanone |
| 2.11% | cyclohexanol |
| 0.4–0.8% | miscellaneous by-product acids, alcohols, aldehydes, esters, etc. |
| balance | cyclohexane |

This organic feed stream was fed to the mixer-reactor system through a preheater (120° C.) at a controlled rate of 798 g/min.

3. Aqueous 15% NaOH solution was fed to the mixer-reactor system through a separate preheater (120° C.) at a controlled rate of 103 g/min. An aqueous $CoSO_4$ solution containing 440 ppm cobalt was metered into the caustic stream at 1 g/min.

4. The organic and aqueous feed streams were continuously fed to the mixer-reactor system described above. Mixing intensity was calculated to produce ca. 100 micron dispersed droplets. Temperature was 121° to 124° C. through the reactor due to the exothermic decomposition of the cyclohexyl hydroperoxide. Samples were withdrawn at ten locations along the reactor length, representing hold-up times of 2.2 to 20.5 seconds.

5. It was observed that ca. 12.3 seconds residence time in the mixer-reactor was required to achieve 99% decomposition of the cyclohexyl hydroperoxide. Analyses of the sample withdrawn at 12.3 seconds, and allowed to separate into organic and aqueous phases, showed 0.005% cyclohexyl hydroperoxide, 1.90% cyclohexanone, and 2.32% cyclohexanol in the organic phase; and, 0.07% cyclohexyl hydroperoxide, 0.07% cyclohexanone, and 0.18% cyclohexanol in the aqueous phase. More complete analyses of the sample removed from the mixer-reactor after 20.5 seconds residence time and then allowed to separate into phases showed:

| | ORGANIC PHASE: |
|---|---|
| 0.004% | cyclohexyl hydroperoxide |
| 0.091% | dicyclohexyl hydroperoxide |
| 1.90% | cyclohexanone |
| 2.31% | cyclohexanol |
| 0.10–0.20% | miscellaneous by-product acids, alcohols, aldehydes, esters, etc. |
| balance | cyclohexane |
| | AQUEOUS PHASE: |
| 0.05% | cyclohexyl hydroperoxide |
| NA | dicyclohexyl hydroperoxide |
| 0.049% | cyclohexanone |
| 0.162% | cyclohexanol |
| 2.0% | miscellaneous by-product acid salt anions |
| 0.217% | $CO_3=$ |
| 5.0% | OH— |
| 7.64% | Na+ |
| balance | water |

I claim:

1. A process for the conversion of cyclohexyl hydroperoxide contained in a mixture with cyclohexane, cyclohexanone, cyclohexanol and aqueous caustic, to cyclohexanone and cyclohexanol, which comprises adding a metal salt that accelerates the decomposition of cyclohexyl hydroperoxide and thereafter subjecting the mixture to turbulent high-intensity mixing to create a dispersed phase drop size of between 50 to 500 microns, for a time of between 3 and 45 seconds at a temperature between 100 to 140 degrees C., and then subjecting the mixture to a non-turbulent decantation.

2. The process of claim 1 in which the turbulent high-intensity mixing takes place in a static mixer, and the dispersed phase drop size is ca. 100 microns.

3. The process of claim 1 in which the metal in the metal salt is selected from the group consisting of cobalt, copper, chromium, iron, and vanadium.

4. The process of claim 3 in which the metal salt concentration is in the range of about 0.1 to about 50 ppm by weight of the mixture.

* * * * *